United States Patent [19]
Raghu et al.

[11] 4,210,760
[45] Jul. 1, 1980

[54] PROCESSES FOR DEHYDROGENATION OF ARYLIMIDAZOLIDONES

[75] Inventors: Sivaraman Raghu, Norwalk; Arthur K. Hoffmann, New Canaan, both of Conn.

[73] Assignee: American Cyanamid Company, Stamford, Conn.

[21] Appl. No.: 958,218

[22] Filed: Nov. 6, 1978

[51] Int. Cl.[2] .......................................... C07D 233/70
[52] U.S. Cl. .................................................... 548/320
[58] Field of Search .............................. 548/320, 335

[56] References Cited
U.S. PATENT DOCUMENTS
2,226,057  12/1940  Graenacher et al. ................ 548/335

OTHER PUBLICATIONS

Hofmann Imidazole and its Derivatives Part I, pp. 60–63 & 226, N.Y., Interscience, 1953.
Ferm et al., Chem. Rev., 1954, vol. 54, p. 605.
Hofmann Imidazole and its Derivatives Part I, pp. 42 & 220, N.Y., Interscience, 1953.

Primary Examiner—Natalie Trousof
Attorney, Agent, or Firm—Harry H. Kline

[57] ABSTRACT

Dehydrogenation processes comprising contacting 1-(2-alkoxyalkyl)-4-aryl-2-imidazolidone with catalysts comprising a noble metal adsorbed on a carrier to produce 1-(2-alkoxyalkyl)-4-aryl-4-imidazolin-2-ones, the dehydrogenation products being useful for synthesis with prochiral catalysts to provide enantiomerically enhanced imidazolidones.

11 Claims, No Drawings

PROCESSES FOR DEHYDROGENATION OF ARYLIMIDAZOLIDONES

BACKGROUND OF THE INVENTION

This invention relates to novel dehydrogenation processes, and more specifically, it relates to the treatment of arylimidazolidones with noble metal catalysts to provide the corresponding arylimidazolinones.

There is a need for the synthesis of various imidazothiazoles since such materials have a number of uses. The synthesis of such materials can also involve the preparation of one or another specific enantiomer. Exemplary of such bicyclic materials is tetramisole, or 2,3,5,6-tetrahydro-6-phenylimidazo[2,1-b]thiazole.

The synthesis of L-(-)-tetramisole, also known as "levamisole", is of great commercial interest because of its great activity as an anthelminthic, as disclosed in U.S. Pat. No. 3,463,786. One newly discovered process for preparing levamisole is a catalytic asymmetric synthesis through reduction of prochiral intermediates. The asymmetric reduction is achieved through catalysis by homogeneous asymmetric rhodium complexes acting on prochiral 1,4-disubstituted-4-imidazolin-2-ones. The maximum enantioselectivity shown was a 33% enantiomeric excess attained with a catalyst system derived from (+)-DIOP and [Rh(COD)]Cl$_2$ acting on 1-(2-methoxyethyl)-3-acetyl-4-phenyl-4-imidazolin-2-one. The reduced product is converted to levamisole with retention of chirality.

Reduction of various substituted prochiral olefins using homogeneous asymmetric complexes of rhodium (I) salts as catalysts is a field that has been extensively examined in recent years. A review of the state of this art by H. B. Kagan has recently appeared in *Pure and Applied Chem.*, 43, 401 (1976). For specific prochiral substrates the degree of enantioselectivity achieved in reduction has been found to be strongly influenced by the choice of the asymmetric tertiary phosphine derivative employed as a ligand in the catalyst complex.

A very high enantioselectivity of 63% enantiomeric excess in a reduced product is attained by catalytic reduction of the aforesaid imidazolin-2-one using a complex derived from (RhCODI)$_2$ and (+)-trans-bis-(1,2-diphenylphosphinomethyl)cyclobutane. The same degree of enantioselectivity has also been attained using the complex derived from [Rh(COD)I]$_2$ and (—)trans bicyclo (2,2,1) bis-(2,3-diphenylphosphinomethyl)heptane.

Maximum enantioselectivity attained through these and related processes is a 63% enantiomeric excess. In other words, the product contains 63% of the S-isomer and 37% of the RS racemate. While these yields permit 63% of the reduced product to be converted to optically pure, physiologically active levamisole, the 37% of racemate would merely produce tetramisole upon reduction, and this would have to be resolved conventionally.

THE INVENTION

It has now been found possible to treat imidazolidones in a novel process to convert them to imidazolinones. This permits further enantioselective synthesis so that an efficient use can be made of the racemate, and it also avoids the necessity of having to resolve racemic tetramisole.

Briefly, the present invention provides processes for the treatment of 1-(2-alkoxyalkyl)-4-aryl-2-imidazolidones having the formula

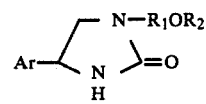

with noble metal catalysts to dehydrogenate Compounds I and produce the corresponding 1-(2-alkoxyalkyl)-4-aryl-4-imidazolin-2-ones having the formula

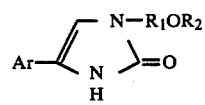

wherein Ar is a mono- or polynuclear aryl or alkyl-substituted aryl group, and R$_1$ and R$_2$ are aliphatic groups. The imidazolinones II can be acylated, hydrogenated with an asymmetric hydrogenation catalyst, and hydrolyzed to obtain imidazolidones having an enantiomeric excess of the desired isomer.

The starting materials I for use in the presently claimed invention are those wherein R$_1$ and R$_2$ are aliphatic radicals, preferably those derived from lower alkyl groups. In desired embodiments of the present invention, R$_1$ is an alkylene group containing from one to four carbon atoms, and R$_2$ is an alkyl group containing from one to four carbon atoms. It will be apparent to those skilled in the art from the present disclosure that when an imidazothiazole is the intended final product, R$_1$ is preferably an ethylene, —CH$_2$—CH$_2$—, group and R$_2$ can have from one to four carbon atoms, with R$_2$ particularly preferred to be a methyl group.

The catalyst used according to the present process is a noble metal which dehydrogenates the imidazolidone ring and produces a carbon-to-carbon double bond between the 4- and 5- carbon atoms. The desirable noble metals for use in the present process include palladium, osmium, iridium, and platinum. It has been found that exceptionally good yields occur with palladium, and this is the preferred noble metal catalyst. It is desirable that the noble metal be in metallic form, that is, as the elemental metal.

It has further been found in practicing the present process that it is desirable to have the noble metal adsorbed on a carrier. Suitable carrier materials include high surface area carbons, clays, earths, and the like. A preferred carrier in certain embodiments is activated charcoal.

The noble metals are used in catalytic amounts, that is, in relatively small quantities, based upon the amounts of imidazolidone. When quantities of the metal are too low, the reaction velocity is greatly slowed, while the use of very large quantities simply causes a recovery problem and can also cause the reaction to proceed too rapidly and to provide undesired by-products. It has been found that amounts of catalyst from about 0.50 to about 2.5 g per mole of imidazolidone provide good results, and are desirable for use herein. In certain preferred embodiments, when the noble metal is adsorbed on a carrier, amounts of from one to ten percent by weight of the carrier are utilized.

The dehydrogenation is desirably carried out in the presence of an inert reaction vehicle. Reaction vehicles which can be used include aliphatic and aromatic liquid hydrocarbons boiling at or below the desired reaction temperatures under the pressures used. Included among such vehicles are saturated aliphatic hydrocarbons such as normal and isomeric heptanes, octanes, nonanes, decanes, and the like and aromatic hydrocarbons such as benzene, toluene, xylene, ethylbenzene, and the like. In certain embodiments, xylenes are the preferred reaction vehicles.

The dehydrogenation reaction is carried out at temperatures providing good reaction velocities while permitting control and minimizing by-products. It has been found that satisfactory rates and facile control of the reaction are obtained with temperatures of from 80° to about 200° C. It is frequently desirable to select a reaction vehicle which can reflux at the reaction temperature.

The dehydrogenation can be carried out over a range of pressures from subatmospheric to superatmospheric. Since the dehydrogenation reaction generates gaseous hydrogen, it is preferred that atmospheric or lower pressures be used. If subatmospheric pressures are used, a less volatile reaction is desirable and can be selected as described above.

In processes for producing imidazothiazoles, imidazolinones II are acylated with carboxylic acid anhydrides to provide 1-(2-alkoxyalkyl)-3-acyl-4-aryl-4-imidazolin-2-ones having the formula

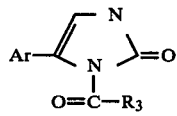
(III)

wherein $R_3$ is a lower alkyl group having from one to five carbon atoms.

The acylation is carried out with dicarboxylic anhydrides having the formula $(R_3CO)_2O$, where $R_3$ has the meaning set forth above. A reaction vehicle can be used or excess anhydride can be used in the reaction. The desirable anhydrides are acetic and butyric anhydrides, and acetic anhydride is especially preferred.

Acylate III is then treated with prochiral catalysts such as the prochiral rhodium complexes to provide 1-(2-alkoxyalkyl)-3-acyl-4-aryl-2-imidazolidones having the formula

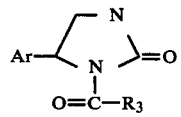
(IV)

where $R_3$ has the meaning set forth above.

These catalyst systems are derived as aforesaid from [Rh(COD)Cl]$_2$, di-$\mu$-chlorobis(1,5-cyclooctadiene)-dirhodium, and (+)-DIOP, isopropylidine dihydroxy-2,3-bis(diphenylphosphino)butane.

Imidazolidone IV is then hydrolyzed to provide the imidazolidone I, having excess of the desired enantiomer. The hydrolysis agent is chosen from among acids and bases, desirably mineral acids and alkali metal hydroxides. The conditions are sufficiently mild so that there is no ring cleavage.

It can thus be appreciated from the present disclosure that the invention permits recovery and reduction of Compounds I so that this by-product can serve again as a starting material. It will be appreciated that the dehydrogenated product II can be combined with fresh material to ensure continuity of the process substantially full recycle of racemic material or material which is relatively not enriched in the desired enantiomer.

The following Examples are given to illustrate embodiments of the invention as it is presently preferred to practice it. It will be understood that these Examples are illustrative, and the invention is not to be considered as restricted thereto except as indicated in the appended Claims.

EXAMPLE I d,1-1-(2-Methoxyethyl)-4-phenyl-2-imidazolidone is obtained by separating this racemic material from an enantiomeric excess of d-enantiomer, and 2 g (0.01 mole) of this material is charged to a 250 ml flask, together with 20 ml xylene. After adding 250 mg of 5% palladium on carbon, the flask contents are heated to reflux and maintained there.

Hydrogen gas is palpably evolved for about one hour, and the refluxing is continued for a total of four hours. It appears that the reaction substantially is complete after about two hours of reflux. The xylene is then removed under reduced pressure. The residue is triturated and filtered.

About 2 g of product is obtained. Infrared (IR) and nuclear magnetic resonance (NMR) spectroscopy confirm that the product is 1-(2-methoxyethyl)-4-phenyl-4-imidazolin-2-one.

The 1-(2-methoxyethyl)phenylimidazolinone so produced is then acylated with acetic anhydride to provide 1-(2-methoxyethyl)-3-acetyl-4-phenyl-4-imidazolin-2-one and this acylate is treated with a prochiral rhodium complex as aforesaid to provide 1-(2-methoxyethyl)-3-acetyl-4-phenyl-2-imidazolidone having an enantiomeric excess of the d-isomer. Hydrolysis of the acylate with aqueous sodium hydroxide provides an enantiomeric excess of the d-isomer of 1-(2-methoxyethyl)-4-phenyl-2-imidazolidone in good yield.

EXAMPLE II

The dehydrogenation of Example I is repeated with 2.3 g (0.01 mole) of 1-(2-ethoxyethyl)-4-phenyl-2-imidazolidone to obtain about 2.1 g of 1-(2-ethoxyethyl)-4-phenyl-4-imidazolin-2-one.

EXAMPLE III

The dehydrogenation of Example I is repeated with 2.5 g (0.01 mole) of 1-(2-butoxyethyl)-4-phenyl-2-imidazolidone to obtain more than 2 g of 1-(2-butoxyethyl)-4-phenyl-4-imidazolin-2-one.

It will be appreciated from the foregoing description that in certain embodiments of the present invention, phenyl is a preferred Ar substituent.

Although the dehydrogenation step is carried out above utilizing a noble palladium metal catalyst, it is within our contemplation to employ an equivalent catalyst in lieu thereof, such as pre-reduced copper chromite or nickel.

We claim:

1. A process for the production of enantiomerically enhanced imidazolidones which comprises the steps of: reacting 1-(2-alkoxyalkyl)-4-aryl-2-imidazolidone in the presence of a noble metal catalyst to dehydrogenate the imidazolidone and provide the corresponding 1-(2-alkoxyalkyl)-4-aryl-2-imidazolinone, reacting the latter with a lower aliphatic carboxylic acid anhydride to produce 1-(2-alkoxyalkyl)-3-acyl-4-imidazolin-2-one, hydrogenating the latter imidazolinone in the presence of a rhodium complex asymmetric catalyst to produce 1-(2-alkoxyalkyl)-3-acyl-4-aryl-2-imidazolidone with an excess of one enantiomer, and hydrolyzing the imidazolidone enhanced in one enantiomer to produce 1-(2-alkoxyalkyl)-4-aryl-2-imidazolidone.

2. A process according to claim 1 wherein the noble metal is palladium.

3. A process according to claim 1 wherein the noble metal is adsorbed on a carrier.

4. A process according to claim 3 wherein the carrier is activated carbon.

5. A process according to claim 1 wherein the dehydrogenation reaction is carried out in the presence of an inert reaction vehicle.

6. A process according to claim 5 wherein the dehydrogenation reaction vehicle is an aliphatic aromatic hydrocarbon.

7. A process according to claim 5 wherein the dehydrogenation reaction vehicle is benzene or an alkyl benzene having from one to three lower alkyl groups.

8. A process according to claim 5 wherin the dehydrogenation reaction vehicle is xylene.

9. A process according to claim 1 wherein the dehydrogenation reaction is carried out at a temperature of from 80° to 150° C.

10. A process according to claim 1 wherein the aryl is phenyl and the alkoxyalkyl is methoxyethyl.

11. A process according to claim 1 wherein the alkoxyalkyl is methoxyethyl.

* * * * *